US010094728B2

(12) United States Patent
Yoshida

(10) Patent No.: US 10,094,728 B2
(45) Date of Patent: Oct. 9, 2018

(54) VACUUM GAUGE AND CONTAMINATION DIAGNOSIS METHOD

(71) Applicant: NATIONAL INSTITUTE OF ADVANCED INDUSTRIAL SCIENCE AND TECHNOLOGY, Tokyo (JP)

(72) Inventor: Hajime Yoshida, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 15/329,986

(22) PCT Filed: Jul. 29, 2015

(86) PCT No.: PCT/JP2015/071563
§ 371 (c)(1),
(2) Date: Jan. 27, 2017

(87) PCT Pub. No.: WO2016/017720
PCT Pub. Date: Feb. 4, 2016

(65) Prior Publication Data
US 2017/0254714 A1 Sep. 7, 2017

(30) Foreign Application Priority Data

Jul. 30, 2014 (JP) .................................. 2014-155291
Jun. 2, 2015 (JP) .................................. 2015-112612

(51) Int. Cl.
*G01L 27/00* (2006.01)
*G01L 21/34* (2006.01)
(Continued)

(52) U.S. Cl.
CPC .............. *G01L 27/00* (2013.01); *G01L 21/34* (2013.01); *G01L 27/007* (2013.01); *H01J 41/06* (2013.01);
(Continued)

(58) Field of Classification Search
CPC ......... G01L 21/00; G01L 21/30; G01L 21/34; G01L 27/00; G01L 27/007; H01J 27/00;
(Continued)

(56) References Cited

U.S. PATENT DOCUMENTS 6,276,343 B1 * 8/2001 Kawamura ........ F02M 25/0809
123/516
6,780,166 B2 * 8/2004 Kanda ................. A61F 9/00736
604/118
(Continued)

FOREIGN PATENT DOCUMENTS

| DE | 102011083136 | 4/2012 |
|---|---|---|
| JP | 2006-344738 A | 12/2006 |
| JP | 5370329 B2 | 12/2013 |

OTHER PUBLICATIONS

International Search Report of the International Searching Authority for International Application No. PCT/JP2015/071563, dated Aug. 25, 2015.
(Continued)

*Primary Examiner* — Hoai-An D Nguyen
(74) *Attorney, Agent, or Firm* — Knobbe, Martens, Olson & Bear, LLP

(57) ABSTRACT

Provided are: a vacuum gauge that, with a simple configuration, can accurately diagnose the degree of contamination of the vacuum gauge; and a contamination diagnosis method that, with a simple process, can accurately diagnose the degree of contamination of a vacuum gauge. Provided is a cold cathode ionization vacuum gauge that has a normal (Continued)

operation mode and a contamination diagnosis mode, the cold cathode ionization vacuum gauge comprising: an anode 1 and a cathode 3 that are for measuring vacuum pressure in the normal operation mode; an anode 7 and the cathode 3 that are for measuring the vacuum pressure in the contamination diagnosis mode; and a controller 10 that compares the size of a current measured between the anode 7 and the cathode 3 and the size of a current measured between the anode 1 and the cathode 3.

9 Claims, 6 Drawing Sheets

(51) Int. Cl.
  *H01J 41/06* (2006.01)
  *H01J 27/02* (2006.01)
  *G01N 27/62* (2006.01)
  *H01J 37/08* (2006.01)
(52) U.S. Cl.
  CPC .............. *G01N 27/62* (2013.01); *H01J 27/02* (2013.01); *H01J 37/08* (2013.01)
(58) Field of Classification Search
  CPC .. H01J 27/02; H01J 37/04; H01J 37/08; H01J 41/00; H01J 41/02; H01J 41/06; G01N 27/62; G01N 27/626; G01N 27/64
  USPC ..... 324/459, 460, 463, 403, 405; 250/222.2, 250/261, 396 R, 397, 398, 423 R, 489, 250/505.1, 506.1, 515.1; 315/108, 315/111.81, 111.91
  See application file for complete search history.

(56) References Cited

U.S. PATENT DOCUMENTS

| | | | |
|---|---|---|---|
| 7,768,267 B2* | 8/2010 | Knott ...................... | H01J 41/02 250/397 |
| 7,795,876 B2* | 9/2010 | Wetzig ................... | H01J 41/06 324/460 |
| 9,588,004 B2* | 3/2017 | Brucker .................. | G01L 21/34 |

OTHER PUBLICATIONS

Supplementary Partial European Search Report issued in corresponding European Patent Application No. 15828187.3 dated Feb. 26, 2018.
Wilfert, S., and C. Edelmann, Inverted Magnetron Manometer With Enhanced Operating Time, Vacuum 82:412-419, 2008.
Supplementary European Search Report issued in corresponding European Patent Application No. 15828187.3 dated Jun. 1, 2018.

* cited by examiner

VACUUM GAUGE AND CONTAMINATION DIAGNOSIS METHOD

CROSS-REFERENCE TO RELATED APPLICATIONS

This application is the U.S. National Phase under 35 U.S.C. § 371 of International Application PCT/JP2015/071563, filed Jul. 29, 2015, which claims priority to JP 2014-155291, filed Jul. 30, 2014 and JP 2015-112612, filed Jun. 2, 2015.

TECHNICAL FIELD

The present invention pertains to a vacuum gauge, and a method of diagnosing a contamination level of the vacuum gauge.

BACKGROUND ART

For example, in a semiconductor manufacturing apparatus, a pressure within a chamber is measured by using a vacuum gauge, and it is, however, known that performance of an ionization vacuum gauge is deteriorated when used in a contaminated environment.

Supposing that the ionization vacuum gauge does not indicate a normal value due to the deterioration, it follows that a large quantity of defective products are produced due to a progress of a semiconductor process under an abnormal condition. At this time, especially in the case of a fault mode in which the value displayed on the ionization vacuum gauge slightly deviates from the normal value, there arises a problem of not being aware of a fault in many cases.
Therefore, a determination of the deterioration has been tried to be made by some methods. Herein, there has hitherto been generally adopted a method of checking soundness of the vacuum gauge by calibrating the vacuum gauge through a test or an examination after removing the vacuum gauge from the semiconductor manufacturing apparatus, and this method has, however, a problem that an operating ratio of the semiconductor manufacturing apparatus drops down because of requiring a considerable length of time and a considerable cost.

A method of making the calibration by introducing a testing gas into a vacuum apparatus does not spread due to an anxiety for contaminating the vacuum apparatus, and due to involving a labor and a cost as well.

Under such circumstances, Patent Document 1 discloses a method of comparing values outputted from two independent vacuum degree detection units based on a same type of principle, and detecting abnormality of the vacuum gauge when a difference therebetween becomes larger than a preset value.

CITATION LIST

Patent Literature

[Patent Literature 1] Japanese Patent Application Laid-Open Publication No. 2006-344738

SUMMARY OF INVENTION

Technical Problem

According to the method described in Patent Document 1, when a fault occurs in one of the two vacuum degree detection units, the abnormality can be promptly detected. However, when the fault occurs not in one but in both of the vacuum degree detection units such as these two vacuum degree detection units being contaminated to a same degree, there is no difference between the output values, resulting in a problem that the abnormality is not detected.

This method is also a method of fitting two gauge heads and therefore requires a large space and two ports for fitting the vacuum gauges.

It is an object of the present invention, which was devised to solve the problems described above, to provide a vacuum gauge capable of highly accurately diagnosing a contamination level of a vacuum gauge with a simple configuration, and a contamination level diagnosis method capable of highly accurately diagnosing the contamination level of the vacuum gauge in a simple procedure.

Solution to Problem

For solving the problems described above, the present invention provides a vacuum gauge having a normal operation mode and a contamination diagnosing mode, including: first pressure sensing means to measure a vacuum pressure in the normal operation mode; second pressure sensing means to measure the vacuum pressure in the contamination diagnosing mode; and comparing means to compare a measurement value by the second pressure sensing means with a measurement value by the first pressure sensing means.

For solving the problems described above, the present invention provides a vacuum gauge having a contamination diagnosing mode and a normal operation mode for measuring a vacuum pressure corresponding to a magnitude of an electric current to be detected, including: a first anode and a first cathode to transfer and receive charged particles forming the electric current; a second anode and a second cathode to transfer and receive the charged particles forming the electric current; and control means to measure the magnitude of the electric current flowing between the first anode and the first cathode by transferring and receiving the charged particles between the first anode and the first cathode in the normal operation mode, to measure the magnitude of the electric current flowing between the second anode and the second cathode by transferring and receiving the charged particles between the second anode and the second cathode in the contamination diagnosing mode, and to compare an electric current magnitude measured between the first anode and the first cathode with the foregoing measured electric current magnitude.

For solving the problems described above, the present invention provides a vacuum gauge having a contamination diagnosing mode and a normal operation mode for measuring a vacuum pressure corresponding to a magnitude of an electric current to be detected, including: a first electrode to collect charged particles forming the electric current; a second electrode to collect the charged particles forming the electric current; and control means to measure the magnitude of the electric current by causing the first electrode to collect the charged particles in the normal operation mode, to measure the magnitude of the electric current by causing the second electrode to collect the charged particles in the contamination diagnosing mode, and to compare an electric current magnitude measured by causing the first electrode to collect the charged particles with the foregoing the electric current magnitude.

For solving the problems described above, the present invention provides a contamination level diagnosis method for a vacuum gauge to measure a vacuum pressure corresponding to a magnitude of an electric current to be detected, including: a first step of transferring and receiving charged particles between a second anode and a second cathode being different from a first anode and a first cathode to transfer and receive the charged particles forming the electric current in a normal operation; a second step of measuring the magnitude of the electric current flowing between the second anode and the second cathode by transferring and receiving the charged particles, and comparing an electric current magnitude measured by transferring and receiving the charged particles between the first anode and the first cathode with the foregoing electric current magnitude; a third step of determining whether a ratio or a difference between the two electric current magnitudes compared in the second step falls within a predetermined range; and a fourth step of diagnosing the vacuum gauge to be clean when making a determination of falling within the predetermined range, and diagnosing the vacuum gauge to be contaminated when making the determination of not falling within the predetermined range in the third step.

For solving the problems described above, the present invention provides a contamination level diagnosis method for a vacuum gauge to measure a vacuum pressure corresponding to a magnitude of an electric current to be detected, including: a first step of causing a second electrode to collect charged particles, the second electrode being different from a first electrode to collect the charged particles forming the electric current in the normal operation; a second step of measuring a magnitude of the electric current by causing the second electrode to collect the charged particles, and to compare an electric current magnitude measured by causing the first electrode to collect the charged particles with the foregoing electric current magnitude; a third step of determining whether a ratio or a difference between the two electric current magnitudes compared in the second step falls within a predetermined range; a fourth step of diagnosing the vacuum gauge to be clean when making a determination of falling within the predetermined range and diagnosing the vacuum gauge to be contaminated when making the determination of not falling within the predetermined range in the third step.

Advantageous Effects of Invention

According to the present invention, it is feasible to provide the vacuum gauge capable of highly accurately diagnosing the contamination level of the vacuum gauge with the simple configuration, and the contamination level diagnosis method capable of highly accurately diagnosing the contamination level of the vacuum gauge in the simple procedure.

DESCRIPTION OF EMBODIMENTS

Figure 1:
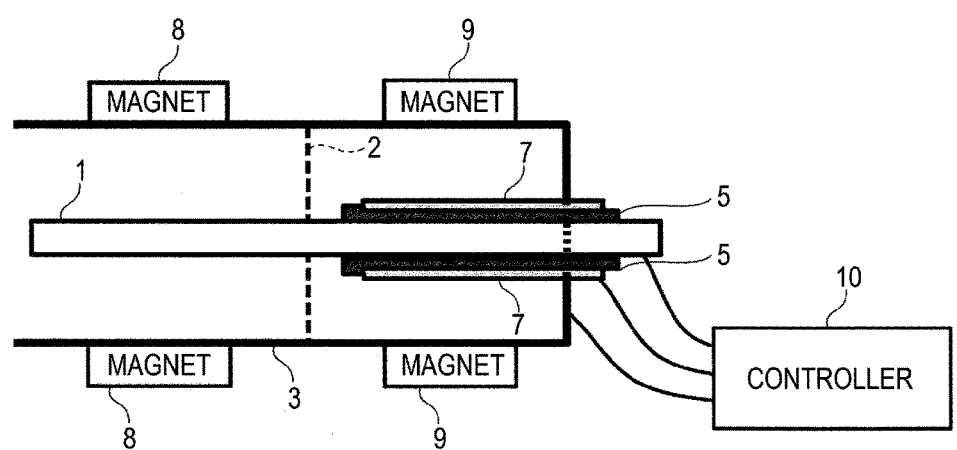
FIG. 1 illustrates a view illustrating a cold cathode ionization vacuum gauge according to an embodiment of the present invention.

An embodiment of the present invention will hereinafter be described in detail with reference to the drawings. Note that the same reference numerals and symbols represent the same or corresponding components in the drawings throughout.

FIG. 1 is a diagram illustrating a configuration of a cold cathode ionization vacuum gauge according to the embodiment of the present invention. As illustrated in FIG. 1, the cold cathode ionization vacuum gauge according to the embodiment of the present invention includes an anode 1, a partition plate 2, a cathode 3, insulators 5, 5, anodes 7, 7, magnets 8, 9, and a controller 10. Herein, the anode 1 and the anode 7 are disposed in a face-to-face relationship with the cathode 3, in which the cathode 3 disposed in the face-to-face relationship with the two anodes 1 and 7 is configured as a common electrode having a same electric potential.

The two anodes 7, 7 and the anode 1 are electrically insulated from each other by the insulators 5, 5 interposed therebetween, and the two anodes 7, 7 are thus interconnected. The anode 1, the anodes 7, 7 and the cathode 3 are connected to the controller 10, whereby the controller 10 controls the electric potentials of the anode 1, the anodes 7, 7 and the cathode 3.

The magnets 8, 8 are provided outwardly of the cathode 3, corresponding to first discharge areas between the anode 1 and the cathode 3; and similarly the magnets 9, 9 are provided outwardly of the cathode 3, corresponding to second discharge areas between the anodes 7, 7 and the cathode 3. These couples of magnets 8, 8 and magnets 9, 9 have functions of applying magnetic fields to electrons released from the cathode 3 and thereby prompting the anodes 1 and 7, 7 to discharge the electricity.

An in-depth description of a contamination level diagnosis method for the cold cathode ionization vacuum gauge illustrated in FIG. 1 will hereinafter be made with reference to FIG. 2.

To start with, a premise is that the cold cathode ionization vacuum gauge has a normal operation mode and a contamination diagnosing mode; the electricity is discharged by the controller 10 between the anode 1 and the cathode 3 in the normal operation mode; and a vacuum pressure is obtained by measuring a magnitude of an electric current flowing between the anode 1 and the cathode 3.

It therefore follows that the anode 1 and the cathode 3 function as a pressure sensing means in the normal operation mode.

On the other hand, in the contamination diagnosing mode for diagnosing the contamination level, at first, in step S1, the controller 10 causes the discharge between the anodes 7, 7 and the cathode 3, whereby the electrons are transferred and received between the anodes 7, 7 and the cathode 3.

Accordingly, it follows that the anodes 7, 7 and the cathode 3 function as the pressure sensing means in the contamination diagnosing mode.

Next in step S2, the controller 10 measures the magnitude of the current flowing between the the anodes 7, 7 and the cathode 3, and compares the thus-measured magnitude of the current with the magnitude of the current measured between the anode 1 and the cathode 3.

Subsequently in step S3, the controller 10 determines whether a ratio or a difference between the electric current magnitudes compared in step S2 falls within a predetermined allowable range.

The controller 10, when making a determination of falling within the allowable range, advances to step S4 and diagnoses the cold cathode ionization vacuum gauge as being clean; and the controller 10, whereas when making a determination of not falling within the allowable range, diverts to step S5 and diagnoses the cold cathode ionization vacuum gauge as being contaminated.

Figure 2:
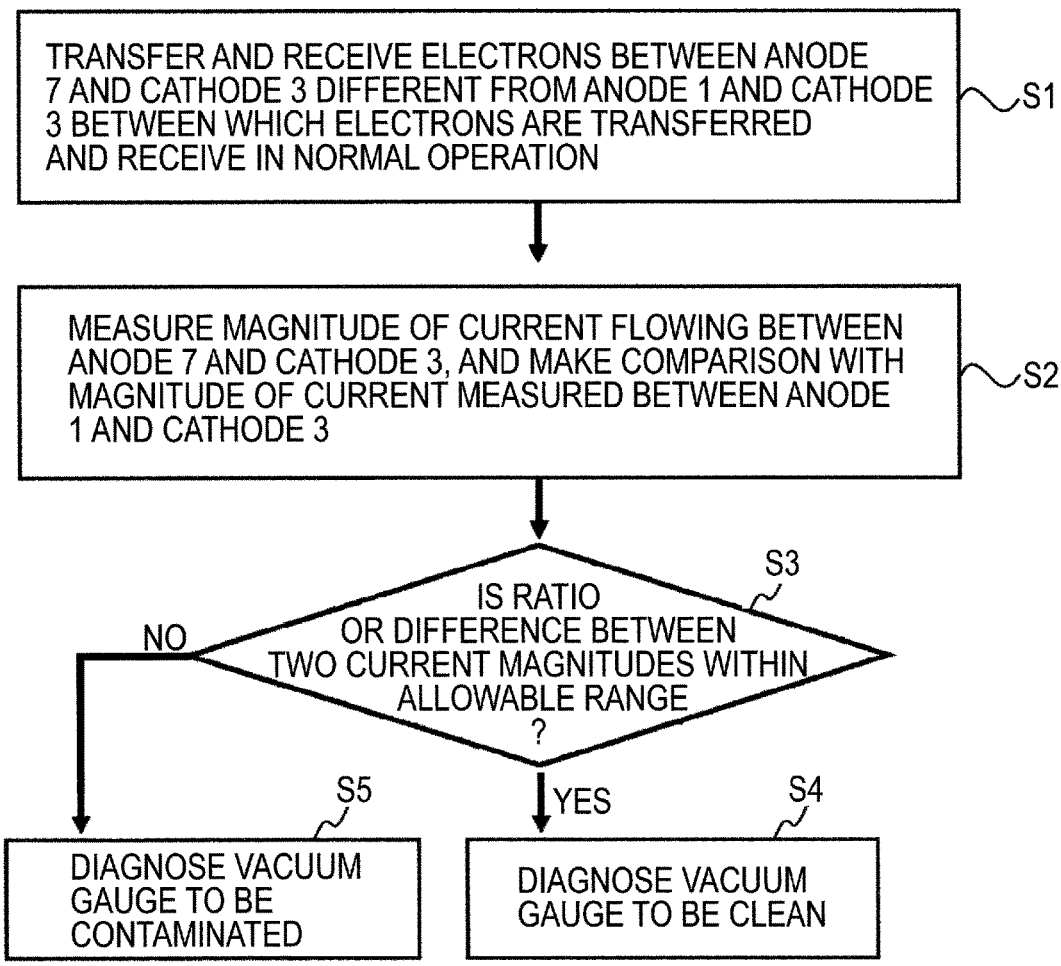
FIG. 2 illustrates a flowchart illustrating a contamination level diagnosis method for the cold cathode ionization vacuum gauge illustrated in FIG. 1.

According to the foregoing contamination level diagnosis method illustrated in FIG. 2, the electrical discharge is not conducted in the normal operation mode in the second discharge area between the anode 7 and the cathode 3 but is conducted only in the contamination diagnosing mode, and hence the vacuum pressure can be measured by using the anode 7 and the cathode 3 that are lower in contamination level than the anode 1 and the cathode 3 configuring the first discharge area used in the normal operation mode.

This method can cause a definite difference between the two current magnitudes set as the comparative targets in step S2 when the anode 1 and the cathode 3 configuring the first discharge area are contaminated.

Note that the contamination diagnosing mode may involve, in addition to discharging only the second discharge area in the description given above, discharging not only the second discharge area but also the first discharge area simultaneously.

Herein, a switchover between the normal operation mode and the contamination diagnosing mode can entail adopting a method of switching off the discharge of any one of the first discharge area and the second discharge area, and thereafter switching on the other discharge area to be discharged.

However, this method has such a problem that the switchover is enabled to be smoothly performed when a pressure of the discharge area is on the order of $10^{-3}$ Pa but is disabled from being performed when the pressure of the discharge area is in ultrahigh vacuum (the pressure is equal to or lower than $10^{-7}$ Pa) because the discharge of the other discharge area is hard to initiate.

Such being the case, when carrying out the switchover, the discharge of one discharge area is kept, while the discharge of the other discharge area is initiated.

With the means such as this, the discharger of the other discharge area is triggered by the discharge kept in one discharge area, i.e., triggered by transferring and receiving charged particles, thereby enabling a smooth initiation of the discharge of the other discharge area.

The normal operation mode and the contamination diagnosing mode can be therefore smoothly switched over by switching off the discharge of one discharge area after initiating the discharge of the other discharge area.

An in-depth description of the embodiment for attaining the switchover between the normal operation mode and the contamination diagnosing mode, will hereinafter be made.

Figure 3:
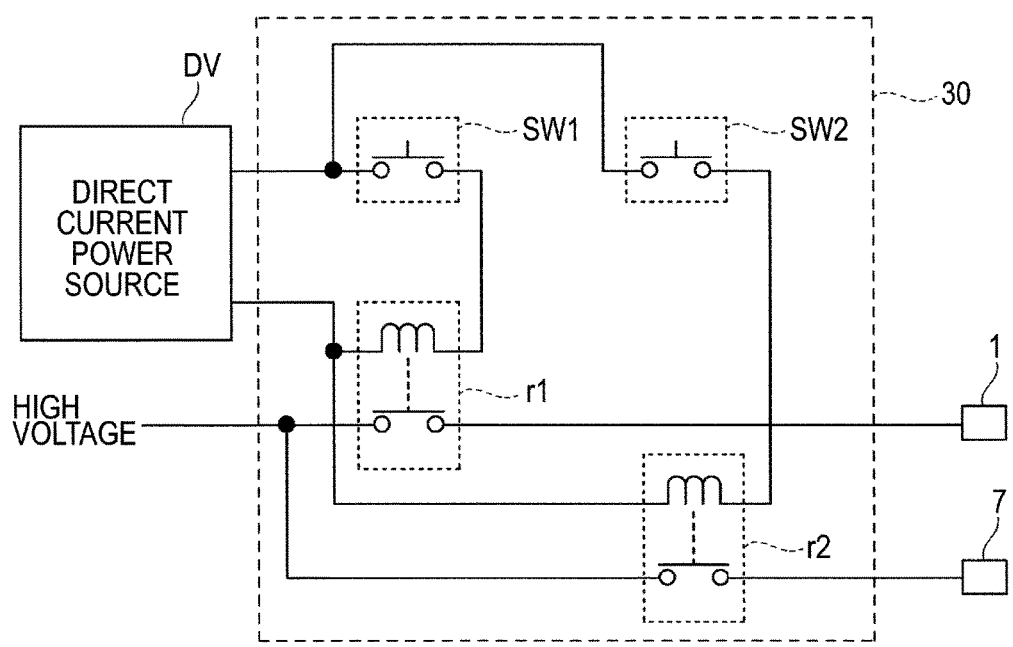
FIG. 3 illustrates a circuit diagram illustrating a configuration of a discharge switchover circuit 30 included by a controller 10 depicted in FIG. 1.

FIG. 3 is a circuit diagram illustrating a discharge switchover circuit 30 included by the controller 10 depicted in FIG. 1. As illustrated in FIG. 3, the discharge switchover circuit 30 includes switches SW1, SW2 and high-voltage relays r1, r2.

Herein, one ends of switches SW1, SW2 and one ends of coils of the high-voltage relays r1, r2 are connected to a direct current power source DV. The other end of the switch SW1 is connected to the other end of the coil of the high-voltage relay r1; and the other end of the switch SW2 is connected to the other end of the coil of the high-voltage relay r2. Both of one ends of switching units of the high-voltage relays r1, r2 are supplied with a voltage as high as about, e.g., 2 kilo volts (kV). The other end of the switching unit of the high-voltage relay r1 is connected to the anode 1, while the other end of the switching unit of the high-voltage relay r2 is connected to the anode 7.

Figure 4:
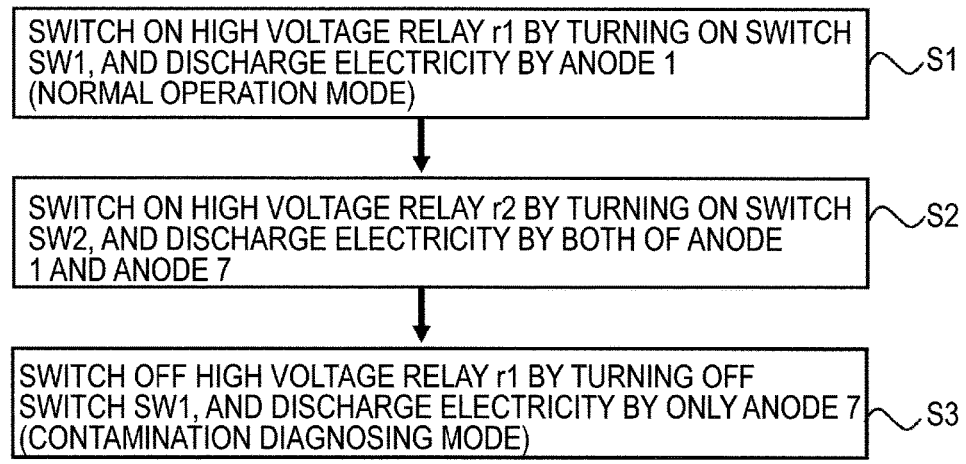
FIG. 4 illustrates a flowchart illustrating the contamination level diagnosis method using the discharge switchover circuit 30 illustrated in FIG. 3.

FIG. 4 is a flowchart illustrating the contamination level diagnosis method using the discharge switchover circuit 30 depicted in FIG. 3. The following discussion will describe in detail the contamination level diagnosis method using the discharge switchover circuit 30 with reference to FIG. 4.

To begin with, in step S1, the high voltage is supplied to the anode 1 by turning on the switch SW1 and thereby switching on the high-voltage relay r1 in the normal operation mode, whereby the discharge takes place between the anode 1 and the cathode 3.

Next, in step S2, the high voltage is supplied to the anode 7 by turning on the switch SW2 and thereby switching on the high-voltage relay r2 while keeping the discharge in step S1, whereby the discharge is initiated between the anode 7 and the cathode 3.

In step S3, the discharge takes place only between the anode 7 and the cathode 3 by turning on the switch SW1 and thereby switching off the high-voltage relay r1 in order to enter the contamination diagnosing mode.

The foregoing contamination level diagnosis method illustrated in FIG. 4 enables the smooth switchover between the normal operation mode and the contamination diagnosing mode by initiating the discharge between the anode 7 and the cathode 3 in the contamination diagnosing mode in a way that makes the use of the discharge state between the anode 1 and the cathode 3 in the normal operation mode. The discharge can be smoothly switched over by performing the same operation even when returned to the normal operation mode from the contamination diagnosing mode after diagnosing the contamination.

Through the operation described above, according to the cold cathode ionization vacuum gauge and the contamination level diagnosis method for the cold cathode ionization vacuum gauge according to the embodiment of the present invention illustrated in FIG. 1, the highly accurate diagnosis of the contamination level can be attained with the simple configuration by the simple method in such a way that the controller 10 separately uses the first discharge area and the second discharge area, provided in one vacuum gauge, in the normal operation mode and the contamination diagnosing mode.

According to the cold cathode ionization vacuum gauge described above, the controller 10 simply switches over the mode to the contamination diagnosing mode without stopping a vacuum apparatus installed with the present vacuum gauge, thereby enabling a determination of soundness of the vacuum gauge and a proper determination of a maintenance timing of the whole vacuum apparatus including the present vacuum gauge.

It follows that the whole vacuum apparatus can be protected from serious contamination by thus ensuring the soundness of the present vacuum gauge.

Figure 5:
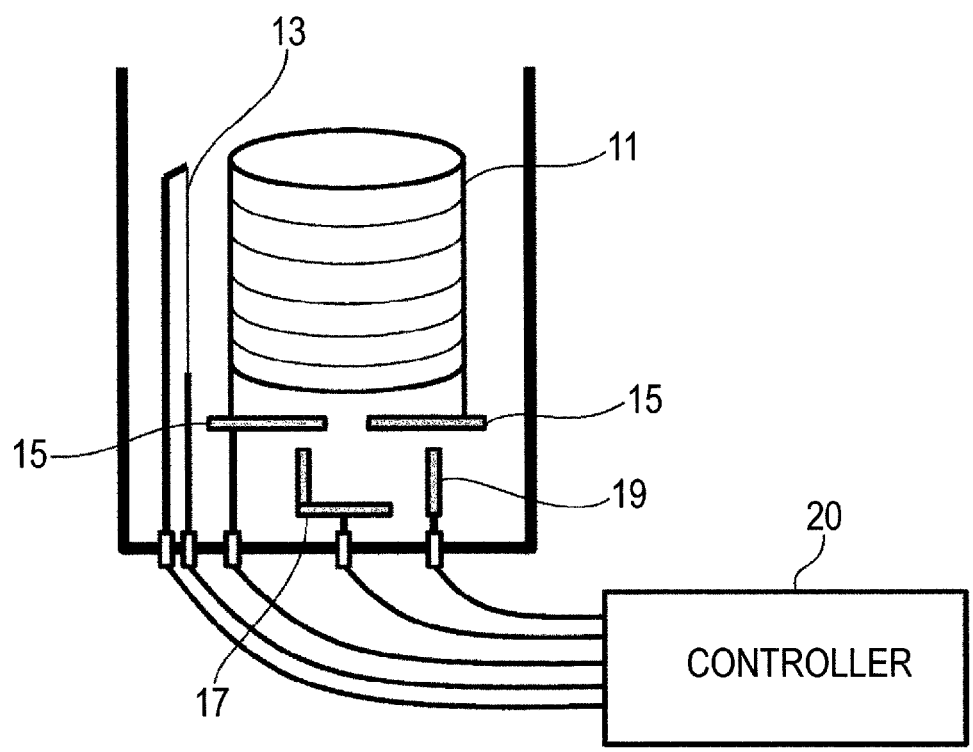
FIG. 5 illustrates a view illustrating a configuration of a hot cathode ionization vacuum gauge according to the embodiment of the present invention.

FIG. 5 is a view illustrating a configuration of a hot cathode ionization vacuum gauge according to the embodiment of the present invention. As illustrated in FIG. 5, the hot cathode ionization vacuum gauge according to the embodiment of the present invention includes a grid (anode)

11, a hot filament (cathode) 13, shields 15, 15, a first ion collector 17, a second ion collector 19, and a controller 20.

Herein, the grid 11 and the hot filament 13 are disposed in the face-to-face relationship, and both of the first ion collector 17 and the second ion collector 19 are disposed on an opposite side to the grid 11 with the shields 15, 15 interposed therebetween. The grid 11, the hot filament 13, the first ion collector 17 and the second ion collector 19 are respectively connect to the controller 20, whereby the controller 20 controls the electric potentials of the grid 11, the hot filament 13, the first ion collector 17 and the second ion collector 19.

A contamination level diagnosis method for the hot cathode ionization vacuum gauge illustrated in FIG. 5 will hereinafter be described in detail with reference to FIG. 6.

In the hot cathode ionization vacuum gauge described above, the electrons released from the hot filament 13 fly to the grid 11, during which the electrons impinge on gaseous molecules to thereby generate positive ions. In the vacuum gauge having the normal operation mode and the contamination diagnosing mode, the first ion collector 17 collects the positive ions in the normal operation mode, and a magnitude of an ion current is measured, thereby obtaining a vacuum pressure.

Accordingly, the first ion collector 17 functions as the pressure sensing means in the normal operation mode.

On the other hand, in the contamination diagnosing mode for diagnosing the contamination level, at first in step S1, the controller 20 deflects a course of the positive ions by setting the first ion collector 17 in a positive potential state, and causes the second ion collector 19 to collect the positive ions.

Accordingly, the second ion collector 19 functions as the pressure sensing means in the contamination diagnosing mode.

Next, in step S2, the controller 20 measures the magnitude of the ion current of the positive ions collected by the second ion collector 19, and causes the first ion collector 17 to collect the positive ions, thereby making a comparison with the measured magnitude of the ion current.

Subsequently in step S3, the controller 20 determines whether a ratio or a difference between the two magnitudes of the ion currents that are compared in step S2 falls within a predetermined allowable range.

The controller 20, when making a determination of falling within the allowable range, advances to step S4 and diagnoses the hot cathode ionization vacuum gauge as being clean; and the controller 10, whereas when making a determination of not falling within the allowable range, diverts to step S5 and diagnoses the hot cathode ionization vacuum gauge as being contaminated.

Note that contaminants are deposited generally on a surface of the ion collector to produce an insulation film concomitantly with the collection of the positive ions, resulting in abnormality of a measured value of the ion current.

Figure 6:
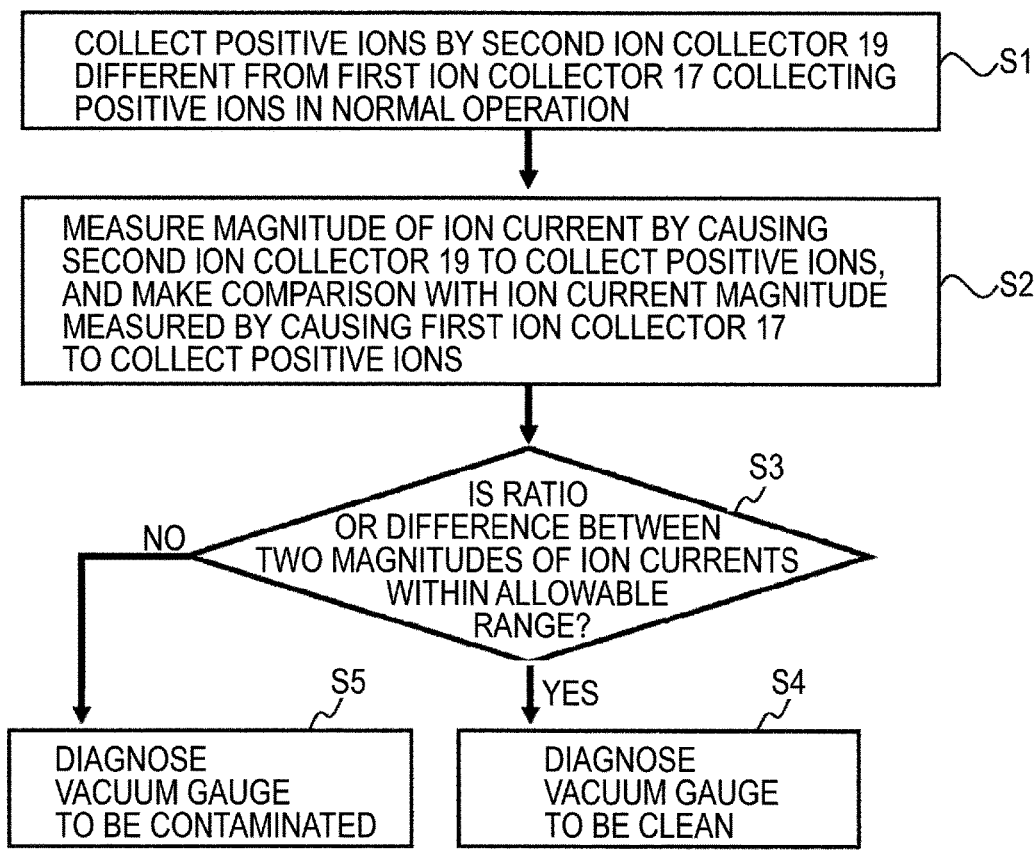
FIG. 6 illustrates a flowchart illustrating a contamination level diagnosis method for the hot cathode ionization vacuum gauge illustrated in FIG. 5.

According to the foregoing contamination level diagnosis method illustrated in FIG. 6, the second ion collector 19 does not collect the ions in the normal operation mode but collects the ions only in the contamination diagnosing mode, and hence the vacuum pressure can be measured by using the second ion collector 19 exhibiting a lower contamination level than on the surface of the first ion collector 17 used in the normal operation mode.

When the first ion collector 17 is contaminated, the definite difference can be thereby caused between the two magnitudes of the ion currents set as the comparative targets in step S2.

Through the operation described above, according to the hot cathode ionization vacuum gauge and the contamination level diagnosis method for the hot cathode ionization vacuum gauge according to the embodiment of the present invention illustrated in FIG. 5, the highly accurate diagnosis of the contamination level can be attained with the simple configuration by the simple method in such a way that the controller 20 separately uses the first ion collector 17 and the second ion collector 19, provided in one vacuum gauge, in the normal operation mode and the contamination diagnosing mode.

By the hot cathode ionization vacuum gauge described above, the controller 20 simply switches over the mode to the contamination diagnosing mode without stopping the vacuum apparatus installed with the present vacuum gauge, thereby enabling the determination of the soundness of the vacuum gauge and the proper determination of the maintenance timing of the whole vacuum apparatus including the present vacuum gauge.

The whole vacuum apparatus can be protected from more serious contamination by thus ensuring the soundness of the present vacuum gauge.

Note that although describing so far the embodiments of the cold cathode ionization vacuum gauge and the hot cathode ionization vacuum gauge, the present invention is considered applicable to different types of vacuum gauges.

REFERENCE SIGNS LIST 1, 7 anode
3 cathode
8, 9 magnet
10, 20 controller
11 grid (anode)
13 hot filament (cathode)
17 first ion collector
19 second ion collector
30 discharge switchover circuit

What is claimed is:

1. A method of diagnosing contamination level for a vacuum gauge by measuring a vacuum pressure corresponding to a magnitude of a detected electric current, comprising:
   causing a second electrode to collect charged particles, the second electrode being different from a first electrode to collect the charged particles forming the electric current in the normal operation;
   measuring a magnitude of the electric current by causing the second electrode to collect the charged particles, and to compare an electric current magnitude measured by causing the first electrode to collect the charged particles with the foregoing electric current magnitude;
   determining whether a ratio or a difference between the two electric current magnitudes compared in the measuring falls within a predetermined range;
   diagnosing the vacuum gauge to be clean when making a determination of falling within the predetermined range and diagnosing the vacuum gauge to be contaminated when making the determination of not falling within the predetermined range.

2. A vacuum gauge having a contamination diagnosing mode and a normal operation mode for measuring a vacuum pressure corresponding to a magnitude of an electric current to be detected, comprising:
   a first anode and a first cathode transferring and receiving charged particles forming the electric current;

a second anode and a second cathode to transferring and receiving the charged particles forming the electric current; and a control unit measuring the magnitude of the electric current flowing between the first anode and the first cathode by transferring and receiving the charged particles between the first anode and the first cathode in the normal operation mode, measuring the magnitude of the electric current flowing between the second anode and the second cathode by transferring and receiving the charged particles between the second anode and the second cathode in the contamination diagnosing mode, and comparing an electric current magnitude measured between the first anode and the first cathode with the foregoing measured electric current magnitude.

3. The vacuum gauge according to claim 2, further comprising a magnetic field applying unit applying magnetic fields to the charged particles transferred and received between the first anode and the first cathode and to the charged particles transferred and received between the second anode and the second cathode.

4. The vacuum gauge according to claim 2, wherein the first cathode and the second cathode are configured as common electrodes having a same electric potential.

5. The vacuum gauge according to claim 2, wherein the control unit, when switching over the normal operation mode and the contamination diagnosing mode, starts transferring and receiving the charged particles in the mode after the switchover while keeping the transfer and the reception of the charged particles in the mode before the switchover.

6. A vacuum gauge having a contamination diagnosing mode and a normal operation mode for measuring a vacuum pressure corresponding to a magnitude of an electric current to be detected, comprising:

a first electrode collecting charged particles forming the electric current;

a second electrode collecting the charged particles forming the electric current; and a control unit measuring the magnitude of the electric current by causing the first electrode to collect the charged particles in the normal operation mode, measuring the magnitude of the electric current by causing the second electrode to collect the charged particles in the contamination diagnosing mode, and comparing an electric current magnitude measured by causing the first electrode to collect the charged particles with the foregoing the electric current magnitude.

7. The vacuum gauge according to claim 6, further comprising an anode and a cathode for generating the charged particles.

8. A method of diagnosing contamination level for a vacuum gauge by measuring a vacuum pressure corresponding to a magnitude of a detected electric current, comprising:

transferring and receiving charged particles between a second anode and a second cathode being different from a first anode and a first cathode to transfer and receive the charged particles forming the electric current in a normal operation;

measuring the magnitude of the electric current flowing between the second anode and the second cathode by transferring and receiving the charged particles, and comparing an electric current magnitude measured by transferring and receiving the charged particles between the first anode and the first cathode with the foregoing electric current magnitude;

determining whether a ratio or a difference between the two electric current magnitudes compared in the measuring falls within a predetermined range; and diagnosing the vacuum gauge to be clean when making a determination of falling within the predetermined range, and diagnosing the vacuum gauge to be contaminated when making the determination of not falling within the predetermined range.

9. The contamination level diagnosis method according to claim 8, wherein the transferring and receiving comprises:

starting the transfer and the reception of the charged particles between the second anode and the second cathode while keeping the transfer and the reception of the charged particles in the normal operation; and finishing the transfer and the reception of the charged particles between the first anode and the first cathode after starting the transfer and the reception of the charged particles between the second anode and the second cathode.

* * * * *